(12) United States Patent
Harrison et al.

(10) Patent No.: US 10,485,944 B2
(45) Date of Patent: Nov. 26, 2019

(54) ADJUSTABLE POSITIVE AIRWAY PRESSURE OR VENTILATION SYSTEM

(71) Applicants: Donald Harrison, Park City, UT (US); Andrew Havens Gosline, Cambridge, MA (US); Veaceslav Gheorghe Arabagi, Cambridge, MA (US); Aaron Jonah Kapelus, Jamaica Plain, MA (US)

(72) Inventors: Donald Harrison, Park City, UT (US); Andrew Havens Gosline, Cambridge, MA (US); Veaceslav Gheorghe Arabagi, Cambridge, MA (US); Aaron Jonah Kapelus, Jamaica Plain, MA (US)

(73) Assignee: HUMAN DESIGN MEDICAL, LLC, North Billerica, MA (US)

( * ) Notice: Subject to any disclaimer, the term of this patent is extended or adjusted under 35 U.S.C. 154(b) by 1140 days.

(21) Appl. No.: 14/800,999

(22) Filed: Jul. 16, 2015

(65) Prior Publication Data
US 2016/0015921 A1    Jan. 21, 2016

Related U.S. Application Data

(60) Provisional application No. 62/025,073, filed on Jul. 16, 2014, provisional application No. 62/025,077, (Continued)

(51) Int. Cl.
*A61M 16/06* (2006.01)
*A61M 16/10* (2006.01)
*A61M 16/00* (2006.01)
*A61M 16/08* (2006.01)
*A61M 16/22* (2006.01)

(52) U.S. Cl.
CPC .... *A61M 16/0683* (2013.01); *A61M 16/0066* (2013.01); *A61M 16/0605* (2014.02); *A61M 16/0622* (2014.02); *A61M 16/0666* (2013.01); *A61M 16/0694* (2014.02); *A61M 16/0816* (2013.01); *A61M 16/0875* (2013.01); *A61M 16/1045* (2013.01); *A61M 16/22* (2013.01); *A61M 2016/0661* (2013.01); *A61M 2205/0216* (2013.01)

(58) Field of Classification Search
CPC ........ A61M 16/00; A61M 16/06–0694; A61M 16/20–209; A61M 16/0003–0012; A61M 16/0015–0042; A61B 9/00; A61B 9/02; A61B 9/027; A62B 7/00; A62B 7/054; A62B 7/18; A62B 18/00; A62B 18/10; B63C 11/12; B63C 11/18
See application file for complete search history.

(56) References Cited

U.S. PATENT DOCUMENTS

| | | | |
|---|---|---|---|
| 6,431,172 B1 * | 8/2002 | Bordewick | A61M 16/0666 128/206.11 |
| 8,402,971 B2 | 3/2013 | Schneider | |

(Continued)

*Primary Examiner* — Tan-Uyen T Ho
*Assistant Examiner* — Ned T Heffner
(74) *Attorney, Agent, or Firm* — Yi Liu

(57) ABSTRACT

The present disclosure relates to a comfortable and adjustable nasal pillow configured to be part of a nasal pillow system that is part of a mask system used with a ventilation or PAP device. The nasal pillows are configured to have multiple degrees of freedom of rotation.

23 Claims, 6 Drawing Sheets

Related U.S. Application Data filed on Jul. 16, 2014, provisional application No. 62/049,994, filed on Sep. 12, 2014.

(56) References Cited

U.S. PATENT DOCUMENTS

| | | | |
|---|---|---|---|
| 2005/0011524 A1* | 1/2005 | Thomlinson | A61M 16/0666 128/207.18 |
| 2009/0095303 A1 | 4/2009 | Sher et al. | |
| 2009/0320851 A1* | 12/2009 | Selvarajan | A61M 16/0683 128/207.13 |
| 2010/0132716 A1* | 6/2010 | Selvarajan | A61M 16/0666 128/207.18 |
| 2011/0232649 A1 | 9/2011 | Collazo et al. | |
| 2012/0204870 A1 | 8/2012 | McAuley et al. | |

* cited by examiner

ADJUSTABLE POSITIVE AIRWAY PRESSURE OR VENTILATION SYSTEM

PRIORITY CLAIM

Priority is claimed to co-pending U.S. Provisional Patent Application Ser. No. 62/025,073, filed Jul. 16, 2014, 62/025,077, filed Jul. 16, 2014, and 62/049,994 filed Sep. 12, 2014 which are hereby incorporated herein by reference in their entirety.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to medical devices, and more particularly to portions of air delivery devices that interact with the nasal passages of users. These air delivery devices may be used with positive airway pressure [PAP] such as continuous positive airway pressure [CPAP] devices, automatic positive airway pressure devices [APAP], variable positive airway pressure devices [VPAP], and bi-level positive airway pressure devices [BPAP].

2. Description of the Prior Art

Nasal pillows exist to be partially inserted into each of a user's nares and form a seal with the nares, which allows for the user to breathe a pressurized stream of air from the ventilator or PAP device. However, present nasal pillows have been known to have deficient seals which allow the pressurized air to escape from around the pillows and thus reduce the effectiveness of the air pressure supply. Additionally current nasal pillows often put a large and unnecessary amount of pressure on the nare region of the user's face in order to be properly held in place and form an adequate seal. Such large pressures are often required due to the limited flexibility of present nasal pillows. As such the combination of a large pressure being applied to a user's nares through an inflexible pillow can result in a large amount of discomfort which can cause insomnia, and/or greatly discourage the user's desire to use a positive air pressure device, which is often prescribed to treat potentially life threatening conditions, such as sleep apnea. As such, the continued improvement of positive air pressure facial interfaces such as masks and pillows is a continuing endeavor.

A need therefore exists for a nasal pillow that is interchangeable with a mask system, flexible, adaptable to a user's nares and facial profile, and reduces pressure applied on the nare region while in use.

SUMMARY OF THE INVENTION

A positive airway pressure assembly having a plurality of nasal pillows configured to interface with, and provide a supply of pressurized gas to, the nares of a user. The positive airway pressure assembly can include a mask frame configured to support each of the nasal pillows, the mask frame receiving a supply of pressurized gas at an inlet and delivering a portion of the pressurized gas to each of the nasal pillows. The nasal pillows can each include a connection interface configured to connect to the mask frame and receive the portion of pressurized gas from the mask frame therethrough. An aperture can be provided on each of the nasal pillows, wherein the aperture is configured to deliver the portion of pressurized gas to one of the user's nostrils or nares.

In some embodiments each nasal pillow can be configured to taper from a narrow upper portion about the aperture to a wider base section about the connection interface forming a conical shape. In some embodiments the cone of each nasal pillow can be provided with an elliptical cross section about the narrow upper portion so as to better conform to the individual shape of the nares of a wide variety of users. The conical shape can also form an elliptical, polygonal or other shape at the base portion of each nasal pillow. In other words the nasal pillows are not limited to a circular cross-section and base portion.

In yet more embodiments the nasal pillows can be provided having an annular side wall forming a central channel through which the pressurized gas can travel. This annular side wall can have a tapering thickness being thinner at the upper portion and thicker at the base portion. Alternatively the annular side wall can be formed of a plurality of strips having a varying thickness or durometer wherein each strip extends from the aperture at the upper portion to the base portion.

In some embodiments an attachment sleeve can be provided for interfacing between the mask frame and each of the nasal pillows. The sleeve can then provide at least one degree of motion between the mask frame and each of the pillows allowing the pillows to rotate about the mask frame by rotating the sleeve. In this embodiment each nasal pillow can be formed having a plurality of annular ribs axially spaced about a lower attachment portion of each nasal pillow, the annular ribs engaging with a corresponding recess located about attachment sleeve. These annular ribs can allow each of the nasal pillows to translate radially outward from the mask frame, i.e. axially with respect to each individual nasal pillow.

Further, and particularly for embodiments with elliptical shaped nasal pillows, each of the nasal pillows can be configured to rotate axially to adjust the angular position of each nasal pillow and achieve the most comfortable angular position for engagement with each user.

In order to interface with the attachment sleeve, each nasal pillow can be provided with an attachment portion in the form of an annular tube, the annular tube having a smaller inner diameter than the wider base section of the cone of each nasal pillow. Between the base portion of the cone and this annular tube an elastic trampoline portion can be provided which is more flexible or has a lower durometer than the cone portion and the attachment portion to allow for a certain degree of flex.

Alternatively the cone and the trampoline portions can be provided with varying thicknesses rather than durometers or materials. In such instances the cone can be provided with a wall thickness of less than 40 mils. Or in yet additional embodiments the cone can be provided with a contoured or curved outer or front surface.

In some instances the fit profile of each cone can be varied by varying the material, durometer or thickness of the cone. In one embodiment a plurality of horizontal or vertical coaxial rings are formed as part of the cone, wherein each coaxial ring has a varying durometer, thickness, or material. It will be appreciated that the portion of the cone which actually contacts the user's skin within or around the nares will often be softer to improve the comfort level for the user, as such, in the varying axial ring embodiment the durometer or thickness of each sequential coaxial ring can increases from the aperture to the wider base portion.

Also contemplated herein is a method of providing a pressurized stream of gas to the airways of a user, the various steps including: obtaining a mask frame configured to support a plurality of nasal pillows, the mask frame receiving a supply of pressurized gas at an inlet, and delivering a portion of the pressurized gas to each of a set of apertures; selecting, from a plurality of different sized nasal pillows, a selected pair of nasal pillow best suited to fit with the nares of an intended user; affixing the selected pair of nasal pillows to the mask frame over the apertures; adjusting an individual pillow height of each pillow of the selected pair of nasal pillows with respect to the frame; adjusting a relative rotation of each pillow of the selected pair of nasal pillows; and affixing the mask frame either through, or in conjunction with the nasal pillows, to the face of the user, in a manner that the nasal pillows engage with the user's nares and provide the supply of pressurized gas to the user's airways.

These and other embodiments form some of the various inventive concepts as contained herein. The individual embodiments as described are not intended to be limiting, but are intended only as illustrative of the various inventive concepts and are not intended to be limiting except as claimed below.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

Reference will now be made to the exemplary embodiments illustrated, and specific language will be used herein to describe the same. It will nevertheless be understood that no limitation of the scope of the invention is thereby intended though the exemplary embodiments discussed, but the examples are for purposes of illustration of the inventive concepts.

DETAILED DESCRIPTION OF THE PREFERRED EMBODIMENT

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below may be combined with one another in any suitable manner and may be adapted and applied to other PAP apparatuses, systems, and methods, including, but not limited to, APAP, VPAP, and BPAP apparatuses, systems, and methods.

The present application seeks to provide a solution to the aforementioned problems by creating an adjustable, comfortable, nasal pillow and mask system that is interchangeable, light-weight, and adaptable to individual users.

Figure 1A:
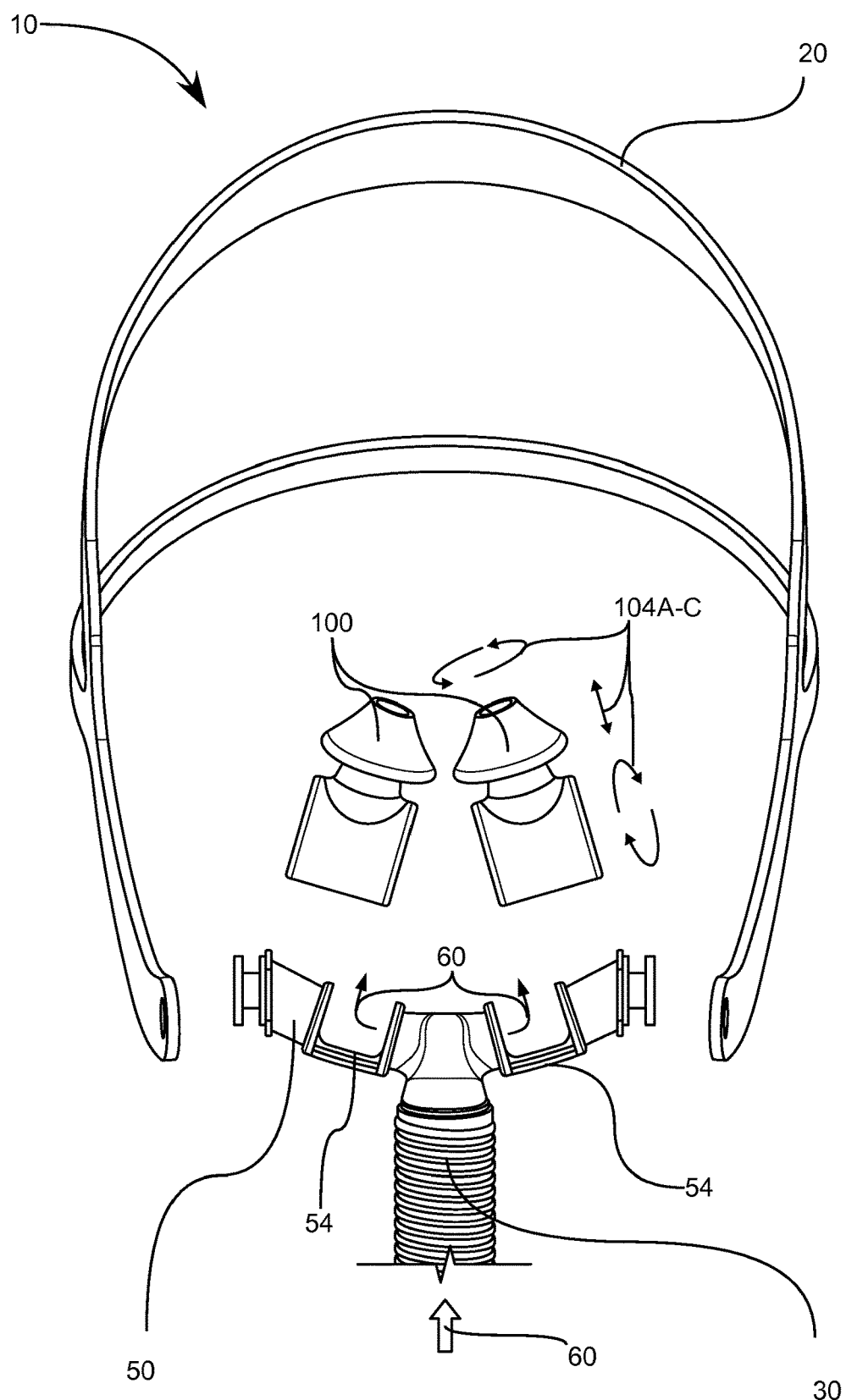
FIGS. 1A-B illustrate partially exploded and assembled views of a positive airway pressure assembly in accordance with various aspects of the present invention.
Figure 1B:
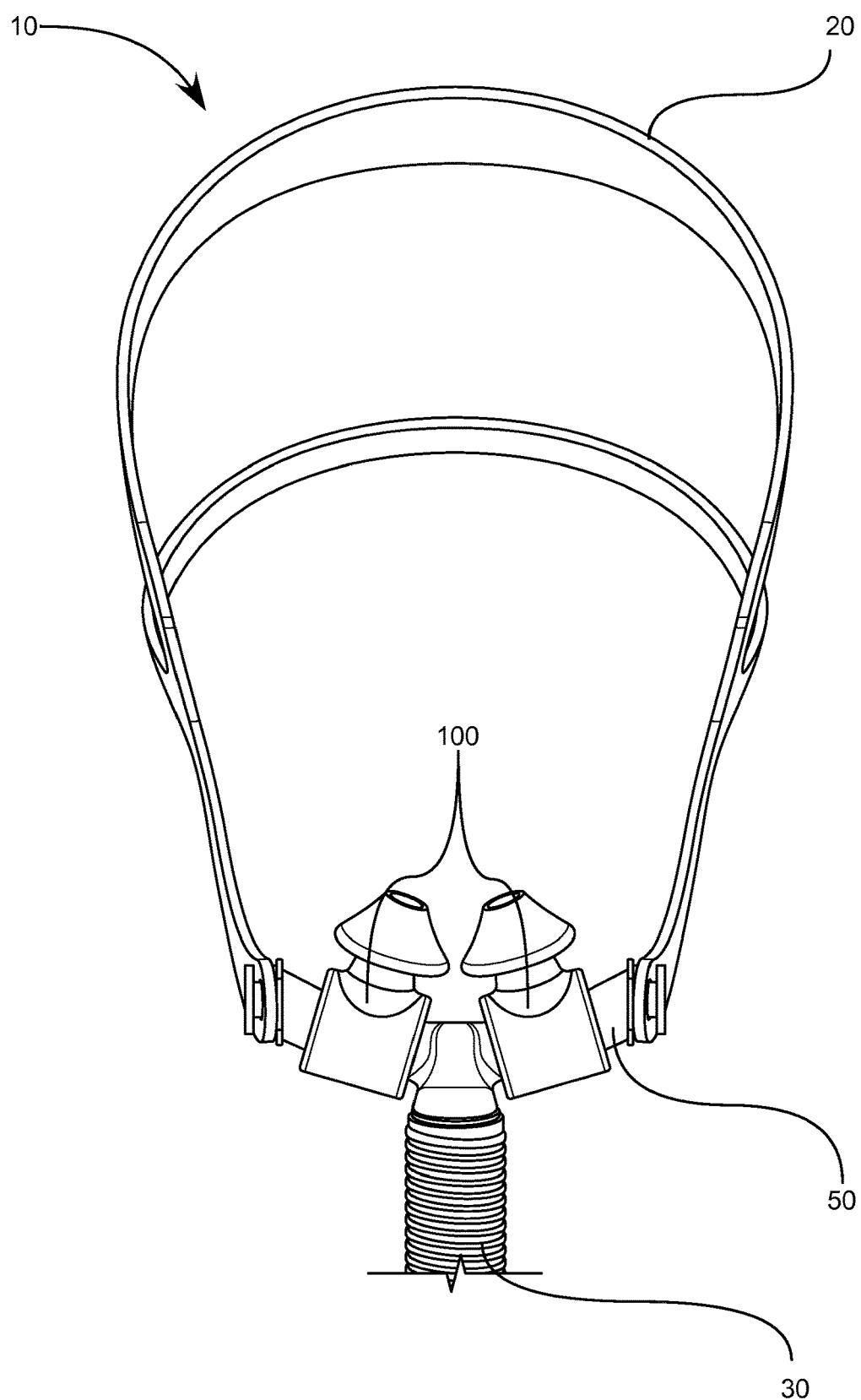

FIGS. 1A-B illustrate a complete positive airway pressure assembly 10 configured to aid in supplying a stream of positive pressure air 60 to the airways of a patient wearing the assembly 10. The assembly includes a mask frame 50 having a pair of nasal pillow assemblies 100 attached thereto. The mask frame 50 receives a stream of pressurized air from a blower (not shown), which can be attached to the mask frame 50 by means of a supply hose 30. The air then travels through the mask frame 50 through apertures 54 and through the associated pillow assemblies 100 to provide air into the nostrils or nares of the user wearing the positive airway pressure assembly 10.

The positive airway pressure assembly 10 can optionally include a headgear system 20 configured to provide a sealing force between the individual pillow assemblies 100 and the nostrils of the user. In certain cases the headgear system 20 can also provide a positioning force between the mask frame 50 and the maxilla of the patient, for example on the portion of the face between the upper lip and below the nose. It will be appreciated that the headgear assembly 20 can be formed of a resilient material, or be adjustable through various means so as to conform to the individual user's contours which, understandably, vary between various users. Further, the headgear assembly 20 and can also be configured to affix to distal ends of the mask frame 50 and can be configured to provide a certain degree of rotational adjustment between the mask frame 50 and the headgear 20.

FIG. 1A also illustrates various degrees of freedom 104 achievable by the illustrated embodiment wherein each individual nasal pillow assembly 100 can rotate about a mask frame axis, the mask frame axis being defined as the axis between a central portion near the inlet and each of the distal ends. Additionally, the pillows can extend radially outward away from the mask frame 50. Finally, each individual pillow can rotate about a pillow axis being defined as an axis extending from the mask frame through a central portion of each nasal pillow assembly 100.

Figure 2A:
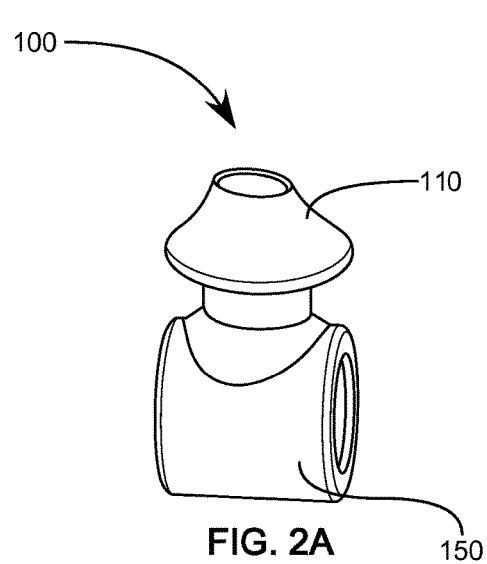
FIGS. 2A-B illustrate assembled and exploded views of a nasal pillow assembly for use in the positive airway pressure assembly of FIGS. 1A-B.
Figure 2B:
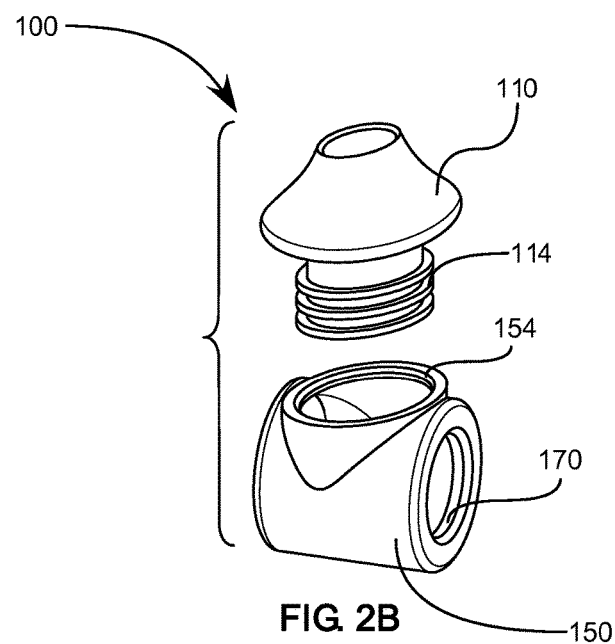

FIGS. 2A-B illustrate assembled and exploded views of the nasal pillow assembly 100 which includes a nasal pillow 110 and attachment sleeves 150. The attachment sleeves 150 in this embodiment are configured to slide over the mask frame 50 and seal over apertures 54, as shown in FIG. 1, to force the air delivered to the mask frame to flow through the pillow assembly 100. The attachment sleeve 150 can be provided with an attachment portion 154 for receiving the pillow 110. The attachment portion 154 can be provided with a series of ribs or channels configured to interface with a plurality of annular ribs 114 and/or channels provided on an annular tube or stem forming an attachment portion of each pillow.

The meshing or integration of the annular ribs 114 with the channels or ribs 154 provided in the attachment sleeve allows for incremental adjustment of the relative height or radial positioning of the nasal pillow 110 with respect to the attachment sleeve 150 by changing which ribs are meshed with which respective channel. In this manner each nasal pillow can translate axially with respect to a pillow axis thus providing one degree of freedom 104A. Additionally, the ribs and channels can slide with respect to one another when twisted about the pillow axis providing a second degree of freedom 104B. Finally, the attachment sleeve 150 can be provided with a sealing lip 170 which is configured to seal against a corresponding seal provided on the mask frame 150. This sealing lip 170 allows for the attachment sleeve 150 to rotate about the mask along the mask frame axis thus providing a third degree of freedom 104C.

Figure 3A:
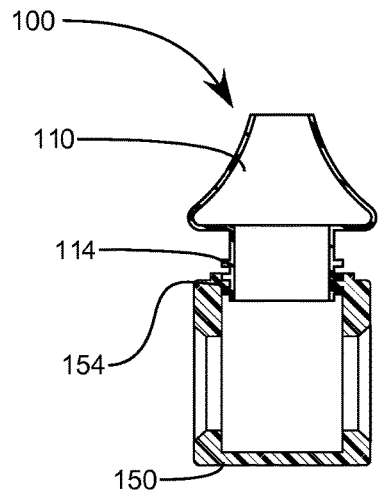
FIGS. 3A-B illustrate cross sectional views of the nasal pillow assembly of FIGS. 2A-B which illustrate an axial translation of an individual nasal pillow.
Figure 3B:
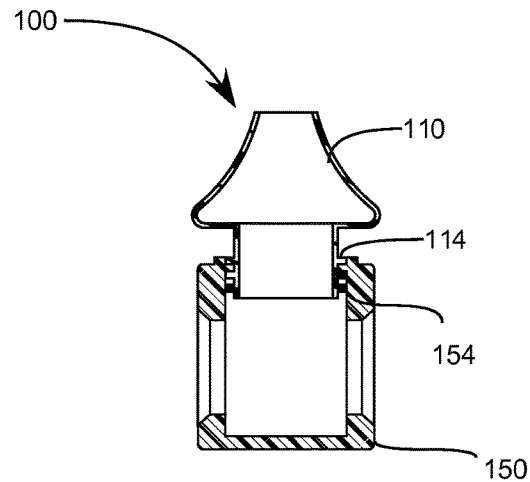
Figure 4:
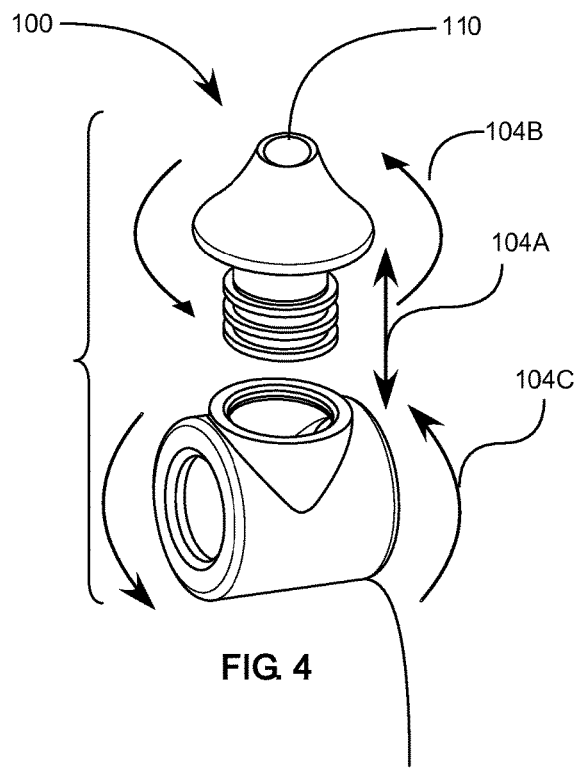
FIG. 4 illustrates a perspective view of the nasal pillow assembly of FIGS. 2A-B which illustrate the degrees of freedom of a nasal pillow with respect to an attachment sleeve.

FIGS. 3A-B and FIG. 4 illustrate different positions relative axial heights of the pillows 110 by incrementally meshing the ribs 114 with the channels 154 of the attachment sleeve 150, where FIG. 3A is a lower relative height and FIG. 3B is a higher relative height along the pillow axis. FIG. 4 shows all three degrees of freedom of each of the separate components as discussed.

Figure 5:
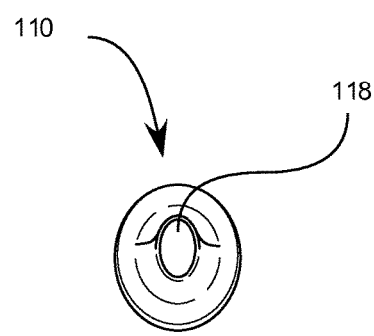
FIG. 5 illustrates a top view of an exemplary nasal pillow for use with the positive airway pressure assembly of FIGS. 1A-B.

FIG. 5 illustrates how the pillow 110 can be provided with an elliptical aperture 118 at a top or point portion which is intended to enter into the nasal passages of the wearing user. The elliptical shape, as illustrated here, is better suited to provide a seal with the nostril walls of the user. One advantage of the second degree of freedom 104B as shown in FIG. 4 is that most users actually have a mostly elliptical nostril opening, and users will have elliptical nostril openings which have varying angular positions with respect to their maxilla. By allowing the second degree of freedom 104B the relative angular position of the ellipse of the nasal pillow 110 can be adjusted so as to match the user's particular nasal openings thus providing better adjustability and customization between users.

In addition, users have differing angular locations and heights of their nasal openings from their maxilla. Thus degrees of freedom 104A and 104C allow for further customization of the relative position of the nasal pillow with respect to the nasal mask frame or attachment sleeve, either of which can be configured to rest against the user's maxilla between the nose and the upper lip.

Figure 6:
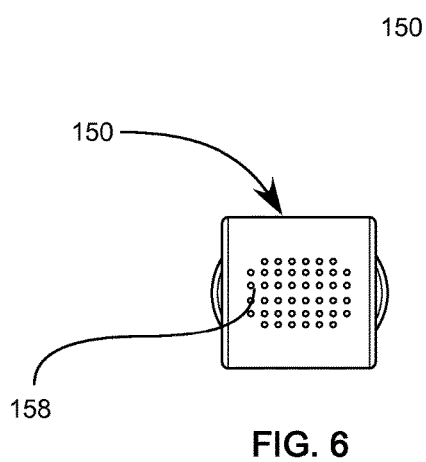
FIG. 6 illustrates a bottom view of an exemplary attachment sleeve for use with the positive airway pressure assembly of FIGS. 1A-B.

FIG. 6 illustrates how the attachments sleeve 150 can be provided with a plurality of washout vents or apertures which allow for expiration of exhaled carbon dioxide when the user exhales. These washout vents can be provided in varying locations, including on the mask frame or at a top portion of the inlet tube, as desired.

Figure 7:
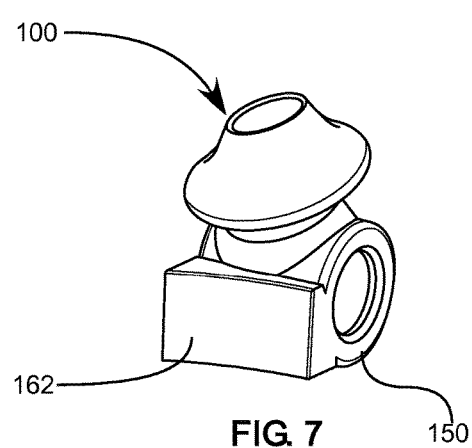
FIG. 7 illustrates an alternative embodiment of an attachment sleeve having a conforming bladder for interfacing with the maxilla of the patient for use with the positive airway pressure assembly of FIGS. 1A-B.

FIG. 7 illustrates an air conform bladder 162 which can be formed as part of the attachment sleeve 150. The air conform bladder 162 can be formed of a malleable material, and have a hollow cavity defined thereby which receives pressurized gas from the interior of the attachment sleeve 150 when attached to the mask frame (not shown here). In this manner, as the pressure rises is increased when the system is on, the air conform bladder is partially inflated and acts similar to a balloon. The air conform bladder 162 can then rest against the maxilla and provide an air cushioned interface between the mask and the user's face.

Figures 10A, 10B, 10C:
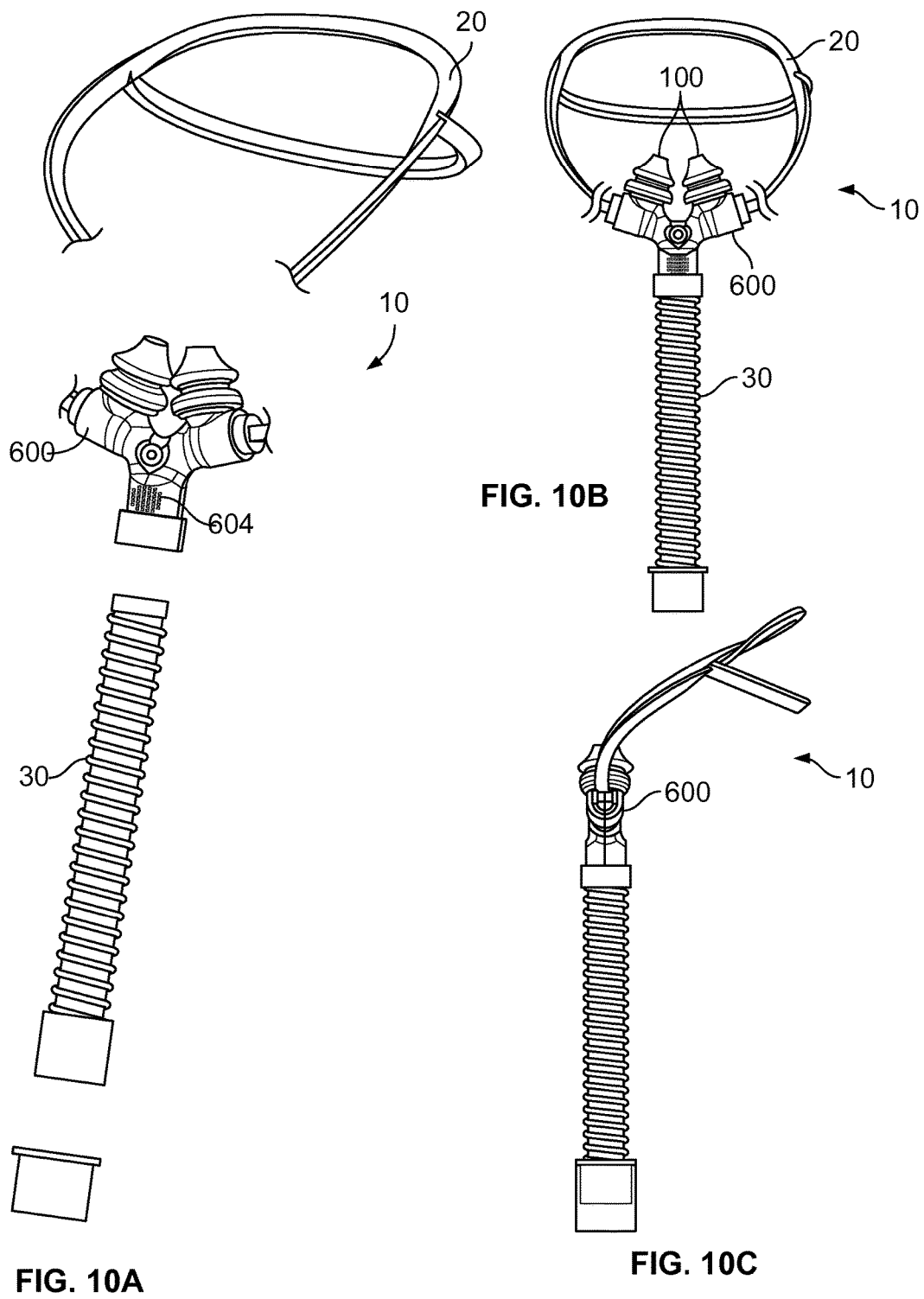
FIGS. 10A-C illustrate exploded side and front views, respectively, of an alternative core or mask frame assembly for use with the ventilation and positive air pressure systems of FIGS. 1A-2B.

In some embodiments (not shown), such as the alternative mask frame in FIGS. 10A-C, an air conform bladder can be configured to be formed as part of each nasal pillow assembly itself or as part of the mask frame.

The shape of the air conforming bladder can be curved having either a concave or convex contact surface, alternatively the contact surface can be angled, rounded or otherwise formed in any other number of desired shapes or with any number of contours so as to best engage with a user's maxilla. The malleable material, similar to the nasal pillows, can also have a varying thickness or durometer.

Figure 8A:
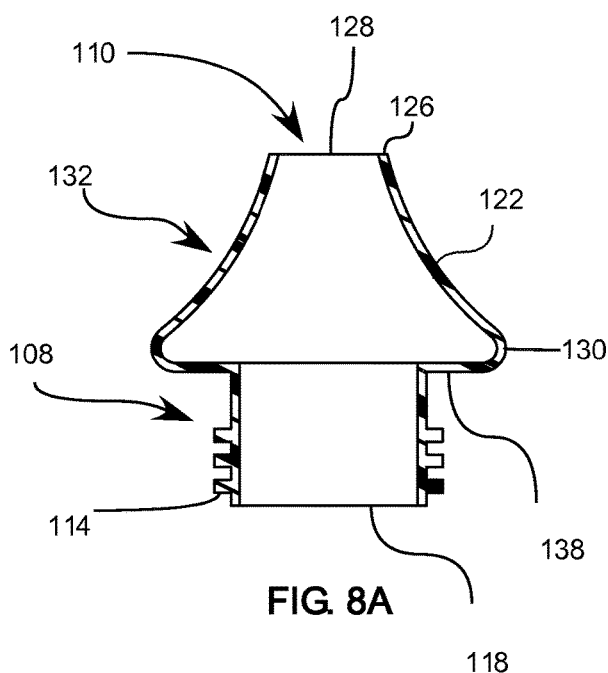
FIGS. 8A-B illustrate cross sectional views of a nasal pillow for use with the positive airway pressure assembly of FIGS. 1A-B in a resting and depressed state.
Figure 8B:
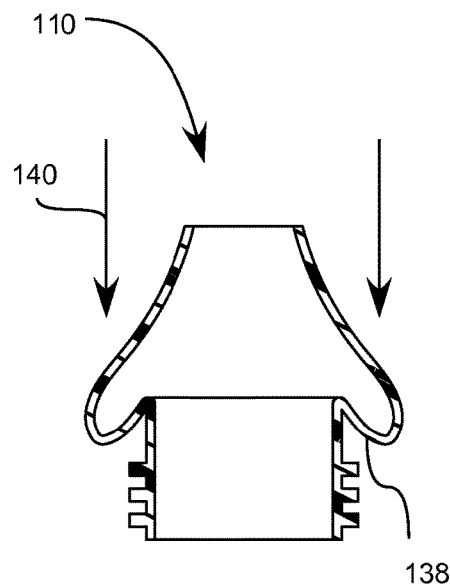

As best seen in FIGS. 8A-B, the nasal pillows 110 can be formed using an annular wall structure to provide an annular cone to interface with the users nares. The annular wall structure can have a narrower top portion 126 and a wider base portion 130 thus forming a cone structure 132 with an opening 128 for allowing air flow through a top or pinnacle of the cone structure. The outer surface or annular wall of the cone structure 132 can have varying contours so as to increase the effectiveness of the seal between the pillow's cone structure 132 and the user's nostrils. The outer surface can be curved in either a concave or a convex shape, or alternatively more complex curvatures, textures, and contours can further be provided.

The cone structure 132 can be attached to a connection interface 108 about a base portion of the nasal pillow. The base portion 108 can include an annular tube 118 with the plurality of ribs 114 as discussed above. The connection interface 108 can be attached to the cone structure using a trampoline portion 138. The trampoline portion 138 can be provided with a thinner wall or an alternative material having greater elasticity so as to allow the trampoline portion 138 to be more flexible than either the cone portion 132 or the connection interface 108. FIG. 8B illustrates how the trampoline portion 138 is allowed to flex when a sealing force is applied by the user's nostrils thus adjusting the sealing force between the nostrils and allowing the sealing force to be indirectly affected by a positioning force provided by the headgear assembly. The trampoline portion can also allow the cone portion to pivot or tilt about the annular tube or stem allowing for additional angles of adjustment. For example, FIG. 8B shows cone deforming about the trampoline portion uniformly, as a force vertically aligned with the cone is applied. However, an off vertical axial force, or alternatively a torsional force, would cause the cone to deform non-uniformly or pivot about the stem. This allows users to further customize the fitting to their individual nares.

Figure 9A:
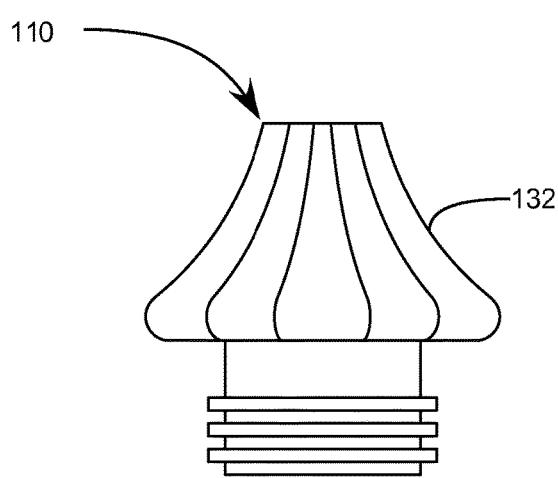
FIGS. 9A-B illustrate side views of various nasal pillows having varying durometer materials, or thicknesses for achieving different user fit profiles.
Figure 9B:
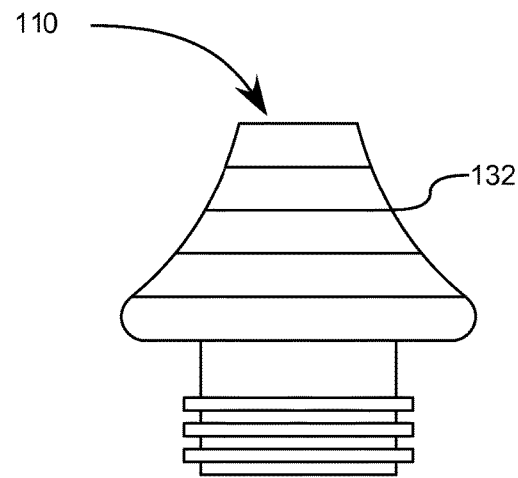

FIGS. 9A-B illustrate how the cone portion 132 of each pillow 110 can be provided using varying thicknesses, durometers, or materials. In some embodiments the cone portion can have a thinner wall or lower durometer at a top portion and a thicker wall or a higher durometer at a base portion to provide increased comfort to the user at the portions that actually contact the inside or walls of the user's nostrils, i.e. the top portion of the cone. In some embodiments, and as shown in FIG. 9A, the cone portion 132 can be provided with a series of strips extending from a top portion to a bottom portion, each strip having varying thickness, durometer, or even varying materials so as to achieve a desired fit or comfort profile. Alternatively, as shown in FIG. 9B the cone portion 132 can be formed using a plurality of annular rings or sections, each ring or section having a different thickness, durometer, or material. In this embodiment the top ring can have a lower durometer value, or be softer than the lowest ring. The intermediate rings can gradually increase in hardness or thickness from a top portion to a base portion.

It will be appreciated that in certain embodiments the headgear can cause a direct tightening of the pillows into the nostrils of the user, thus having a direct correlation to a sealing force. In yet other embodiments, for example, when providing an air conform bladder, as discussed with reference to FIG. 7, the force applied by the headgear can be partially directed through the air conform bladder and into the maxilla to provide a primarily a positioning force, where the sealing force can be adjusted by changing the relative placement of the mask frame on the face, which is held by the positioning force. In yet additional embodiments, the nasal pillows can be caused to enter into, and hold their relative position by the elastic properties of the pillows being exerted onto the inner walls of the user's nostrils or nares without the use of headgear altogether.

The cone portion, attachment portion and the trampoline portions, as discussed above, can have varying thicknesses in the range of about 10 mils to approximately 40 mils.

In another embodiment, (not shown) the air conform bladder or cushion portion can also be filled with a foam or spongy material. This may be completely encapsulated within the sleeve or attached to the mask. In some versions the foam is open to internal air flow and pressure within the mask system. Similar to the air conforming bladder, the foam can also be shaped to fit a user's facial profile and more specifically in the area beneath the nose. It is contemplated to have detachable or interchangeable cushions of shapes and sizes to accommodate the facial features of different users.

FIGS. 10A-C illustrate an alternative embodiment of a mask frame 600. This mask frame is more rigid and instead of interfacing with the nasal pillow assembly 100 using a rotatable sleeve, the arms of mask frame 600 are rigid and do not provide rotation of the pillow assemblies 100 about the respective arm portions. This embodiment provides increased stability for headgear attachment and facial placement purposes. In this embodiment the nasal pillows are still permitted to rotate about the pillow's central axis, wherein the pillows can have an elliptical cross section. Height adjustability of each nasal pillow is also possible with some versions of mask frame 600.

The arms extending from the mask frame 600 as shown are angled and as a user rotates an elliptical-cross-sectioned nasal pillow about its axis, the angle at which the nasal pillow engages a user's nares varies. This adjustability can help a user optimize or customize the fitting to their choosing. As mentioned, the trampoline portion of the base about which the nasal pillows are formed can also deform and pivot about the stem allowing the user to customize the fit.

The rotation, non-circular cone, and pivoting features all work together to allow a customizable fit.

In this embodiment a plurality of washout vents 604 can be provided in a central portion of the mask frame 600. Additionally, the headgear 20 can be attached to the mask frame 600 using any of the previously discussed headgear attachment interfaces.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Further, discussion with regard to any of the specific features is intended to be for illustrative purposes, with the understanding that any feature discussed herein can be used in combination with any number of other features in any combination from any of the various embodiments. Accordingly, it is not intended that the invention be limited, except as by the claims set forth below.

We claim:

1. A positive airway pressure assembly, the assembly comprising:
    a plurality of nasal pillows;
    a mask frame comprising a central portion and a distal portion, wherein the central portion and distal portion defines a mask frame axis;
    wherein each nasal pillow comprises:
        a connection interface configured to connect to the mask frame; and
        an aperture;
            Wherein each nasal pillow comprises an upper portion and a base portion, wherein the nasal pillow tapers from the narrow upper portion about the aperture to the wider base section forming a cone;
            wherein the connection interface extends from the base portion; and
            wherein each of the nasal pillows is configured to independently rotate about the mask frame axis.

2. The positive airway pressure assembly of claim 1, wherein each of the nasal pillows has an elliptical cross section about the narrow upper portion.

3. The positive airway pressure assembly of claim 1, wherein the cone has a wall thickness of less than 20 mils.

4. The positive airway pressure assembly of claim 1, wherein the cone has a curved front surface.

5. The positive airway pressure assembly of claim 1, wherein the cone is formed of a plurality of coaxial rings, each coaxial ring having a varying durometer.

6. The positive airway pressure assembly of claim 1, wherein each of the nasal pillows has an annular sidewall.

7. The positive airway pressure assembly of claim 6, wherein the annular side wall of the cone has a tapering thickness being thinner at the upper portion and thicker at the base portion.

8. The positive airway pressure assembly of claim 6, wherein the annular side wall of the cone has a constant thickness with a varying durometer between the upper portion and the base portion.

9. The positive airway pressure assembly of claim 6, wherein the annular side wall has a plurality of strips having a varying thickness, each strip extending from the aperture at the upper portion to the base portion.

10. The positive airway pressure assembly of claim 1, comprising an attachment sleeve for interfacing between the mask frame and each of the nasal pillows.

11. The positive airway pressure assembly of claim 10, wherein each nasal pillow is provided with a plurality of annular ribs axially spaced about an attachment portion of each nasal pillow, the annular ribs engaging with a corresponding recess located about the attachment sleeve.

12. The positive airway pressure assembly of claim 10, wherein the attachment sleeve can rotate axially with respect to the mask frame.

13. The positive airway pressure assembly of claim 10, comprising an air conforming bladder extending from the attachment sleeve and configured to engage a user's maxilla.

14. The positive airway pressure assembly of claim 10, wherein each of the nasal pillows is configured to rotate axially with respect to the attachment sleeve and wherein each of the nasal pillows is also configured to translate axially with respect to the attachment sleeve.

15. The positive airway pressure assembly of claim 14, wherein the attachment sleeve can rotate axially with respect to the mask frame.

16. The positive airway pressure assembly of claim 10, wherein the base portion of each nasal pillow comprises an annular tube, the annular tube having a smaller inner diameter than the wider base section of each nasal pillow.

17. The positive airway pressure assembly of claim 16, wherein the annular tube interfaces with the base portion of each nasal pillow with an elastic trampoline portion.

18. The positive airway pressure assembly of claim 17, wherein the elastic trampoline portion has a durometer that is lower than the durometer of the annular tube and the cone.

19. The positive airway pressure assembly of claim 17, wherein the elastic trampoline portion has a wall thickness lower than the wall thickness of the annular tube and the cone.

20. The positive airway pressure assembly of claim 1, wherein the connection interface of each nasal pillow is provided with a plurality of annular ribs axially spaced about an attachment portion of each nasal pillow, the annular ribs engaging with a corresponding recess located about the mask frame.

21. The positive airway pressure assembly of claim 20, wherein each of the nasal pillows is configured to rotate about and translate axially with respect to recess located about the mask frame.

22. The positive airway pressure assembly of claim 20, comprising an air conforming bladder extending from the attachment sleeve and configured to engage a user's maxilla.

23. A positive airway pressure assembly, the assembly comprising:
   a plurality of nasal pillows;
   a mask frame comprising a central portion and a distal portion, wherein the central portion and distal portion defines a mask frame axis;
   wherein each nasal pillow comprises:
      a connection interface configured to removably connect to the mask frame;
      a non-circular aperture;
      a flexible base portion that is wider than and engages the connection interface;
      a cone portion extending from the base portion and tapering to a narrow upper portion about where the non-circular aperture is formed; and
         wherein each of the nasal pillows is configured to independently rotate about the mask frame axis.

\* \* \* \* \*